US010485895B2

(12) United States Patent
Tavakol et al.

(10) Patent No.: US 10,485,895 B2
(45) Date of Patent: Nov. 26, 2019

(54) SELF-ASSEMBLING PEPTIDE SCAFFOLDS

(71) Applicants: Shima Tavakol, Tehran (IR); Behnaz Tavakol, Tehran (IR); Amin Almasi, Tehran (IR); Seyed Mahdi Rezayat Sorkhabadi, Tehran (IR)

(72) Inventors: Shima Tavakol, Tehran (IR); Behnaz Tavakol, Tehran (IR); Amin Almasi, Tehran (IR); Seyed Mahdi Rezayat Sorkhabadi, Tehran (IR)

(73) Assignees: Shima Tavakol, Tehran (IR); CELLULAR AND MOLECULAR RESEARCH CENTER, IRAN UNIVERSITY OF MEDICAL SCIENCES, Tehran (IR)

( * ) Notice: Subject to any disclaimer, the term of this patent is extended or adjusted under 35 U.S.C. 154(b) by 0 days.

(21) Appl. No.: 15/633,549

(22) Filed: Jun. 26, 2017

(65) Prior Publication Data
US 2017/0290951 A1    Oct. 12, 2017

Related U.S. Application Data

(60) Provisional application No. 62/374,928, filed on Aug. 15, 2016.

(51) Int. Cl.
| | | |
|---|---|---|
| *A61K 45/06* | (2006.01) | |
| *A61K 47/06* | (2006.01) | |
| *A61K 47/10* | (2017.01) | |
| *A61K 47/26* | (2006.01) | |
| *A61K 6/00* | (2006.01) | |
| *A61K 6/08* | (2006.01) | |
| *A61K 6/04* | (2006.01) | |
| *A61K 6/02* | (2006.01) | |
| *A61K 8/64* | (2006.01) | |
| *A61K 47/42* | (2017.01) | |
| *C07K 7/06* | (2006.01) | |
| *A61L 27/22* | (2006.01) | |
| *A61L 27/54* | (2006.01) | |
| *A61K 31/137* | (2006.01) | |
| *A61K 36/886* | (2006.01) | |
| *A61K 9/107* | (2006.01) | |
| *A61K 9/00* | (2006.01) | |

(52) U.S. Cl.
CPC .......... *A61L 27/22* (2013.01); *A61K 9/0024* (2013.01); *A61K 9/107* (2013.01); *A61K 31/137* (2013.01); *A61K 36/886* (2013.01); *A61K 45/06* (2013.01); *A61K 47/06* (2013.01); *A61K 47/10* (2013.01); *A61K 47/26* (2013.01); *A61L 27/54* (2013.01); *A61L 2300/41* (2013.01); *A61L 2300/426* (2013.01); *A61L 2400/06* (2013.01)

(58) Field of Classification Search
CPC .............. A61K 2300/00; A61K 31/137; A61K 36/886; A61K 45/06; A61K 47/06; A61K 47/10; A61K 47/26; A61K 9/0024; A61K 9/107; A61K 47/48; A61K 6/00; A61K 6/08; A61K 6/04; A61K 8/64; A61K 6/02; A61K 47/42; C07K 7/06; A61L 2300/41; A61L 2300/426; A61L 2400/06; A61L 27/22; A61L 27/54
USPC ............................... 514/18.6, 21.6; 530/327
See application file for complete search history.

(56) References Cited

U.S. PATENT DOCUMENTS

| | | | |
|---|---|---|---|
| 8,741,833 B2 | 6/2014 | Kumada et al. | |
| 2011/0251128 A1* | 10/2011 | Bock-Marquette | ........................ C07K 5/1008 514/16.4 |
| 2012/0213837 A1* | 8/2012 | Botchwey, III | ...... A61K 31/138 424/423 |
| 2013/0089594 A1 | 4/2013 | Anderson et al. | |
| 2015/0099751 A1* | 4/2015 | Mosli | ................... A61K 9/1075 514/243 |

FOREIGN PATENT DOCUMENTS

EP    2711025 A3    9/2014

OTHER PUBLICATIONS

Chun et al, "Mechanism of Action of Oral Fingolimod (FTY720) in Multiple Sclerosis," Clin Neuropharmacol., 2010, 33(2): 91-101.*
Semino, Self-assembling peptides: from bio-inspired materials to bone regeneration, Journal of Dental Research, 2008, pp. 606-616, vol.-issue 87(7).
Koutsopoulos, Controlled release of functional proteins through designer self-assembling peptide nanofiber hydrogel scaffold, Proceedings of the National Academy of Sciences, 2009, pp. 4623-4628, vol.-issue 106(12).
Song, Regeneration of chronic myocardial infarction by injectable hydrogels containing stem cell homing factor SDF-1 and angiogenic peptide Ac-SDKP, Biomaterials, 2014, p. 2436-2445, vol.-issue 35(8).
Huang, Local delivery of FTY720 accelerates cranial allograft incorporation and bone formation, Cell and Tissue Research, 2012, pp. 553-566, vol.-issue 347(3).
Suganya, Aloe vera incorporated biomimetic nanofibrous scaffold: a regenerative approach for skin tissue engineering, Iranian Polymer Journal, 2014, pp. 237-248, vol.-issue 23(3).

* cited by examiner

*Primary Examiner* — Julie Ha
(74) *Attorney, Agent, or Firm* — NovoTechIP International PLLC

(57) ABSTRACT

A mixture for an injectable scaffold may include a self-assembling core and an additive. The additive may include an angiogenic agent, a small molecule drug, and/or an anti-inflammatory agent. The scaffold can be applied to sites where bone growth is desired.

7 Claims, 7 Drawing Sheets

Specification includes a Sequence Listing.

```
┌─────────────────────────────────────────────────────┐
│ Dissolving a self-assembling core in a solvent to form a │──101
│                  first solution                     │
└─────────────────────────────────────────────────────┘
                          │
                          ▼
      ┌──────────────────────────────────────┐
      │ Preparing a nanoemultion of Fingolimod │──102
      └──────────────────────────────────────┘
                          │
                          ▼
┌─────────────────────────────────────────────────────┐
│ Mixing the first solution with the nanoemultion of  │──103
│ Fingolimod and an additive to form a second solution │
└─────────────────────────────────────────────────────┘
                          │
                          ▼
      ┌──────────────────────────────────────┐
      │ Applying the second solution to a defect site to │──104
      │                form a gel             │
      └──────────────────────────────────────┘
```

SELF-ASSEMBLING PEPTIDE SCAFFOLDS

CROSS REFERENCE TO RELATED APPLICATION

This application claims the benefit of priority from U.S. Provisional Patent Application Ser. No. 62/374,928, filed on Aug. 15, 2016, and entitled "AN OSTEOGENIC AND ANGIOGENIC COCKTAIL," which is incorporated herein by reference in its entirety.

TECHNICAL FIELD

The present disclosure generally relates to the field of tissue engineering and in-situ scaffolds, particularly to self-assembling peptide scaffolds, and more particularly to a method for preparing self-assembling peptide scaffolds.

BACKGROUND

Bone loss can be caused by stress shielding, osteolysis, infection, mechanical motion generated from a loose implant, or other injuries or disease. Generally, bone defects can refer to a lack of bone tissue in a body area, where bone should normally be. Bone defects can result after a pathological process has destroyed vital components of the bone. In some cases, extensive trauma and infection can cause bone defects. Damage to the bone and soft tissues typically heals slowly and restitution can be only gradually expected. Bone defects can be treated by various surgical methods.

Two of the most problematic issues in orthopedics are infection in the fracture and surgery sites and poor angiogenesis in the graft or implanted sites that result in failed osteogenesis. Generally a collagen gel is used as a scaffold in the field of regenerative medicine. However, as the collagen gel is derived from an animal, it may cause various infectious diseases. Scaffolds that are derived from a chemically synthesized material and include self-assembling peptides may be used to reduce concerns regarding infectious diseases.

Self-assembling peptide hydrogels are injectable because they can be formed in-situ upon interaction of the peptide solution with biological fluids in a sol-gel process. Self-assembling peptide hydrogels are biocompatible, amenable to molecular design, non-toxic, biodegradable, and applicable to localized therapies through injection to a particular tissue.

For applications of these peptide scaffolds involving implantation into the body, there remains a need in the art for peptide scaffolds that elicit no or minimal immune or inflammatory response, and improve the angiogenesis and osteogenesis of the damaged tissue.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure is directed to a mixture for an injectable scaffold. The mixture may include a self-assembling core and an additive. The additive may be selected from an angiogenic agent, a small molecule drug, and an anti-inflammatory agent.

The above general aspect may include one or more of the following features. For example, the self-assembling core may be selected from (RADA)4 peptide (SEQ ID NO: 1), KSL peptide (SEQ ID NO: 2), EAK peptide (SEQ ID NO: 3), KQL peptide (SEQ ID NO: 4), ESL peptide (SEQ ID NO: 5), EQL peptide (SEQ ID NO: 6), or combinations thereof. In another example, the self-assembling core includes a plurality of self-assembling peptide nanofibers. Moreover, in some cases, the concentration (weight/volume) of the self-assembling core may be between about 0.125 (w/v) and 2 (w/v) of the volume of the whole mixture. In another implementation, the angiogenic agent may be selected from a peptide with an amino acid sequence of seryl-aspartyl-lysyl-proline (SDKP) (SEQ ID NO: 7), VEGF (SEQ ID NO: 8), PGE1 (SEQ ID NO: 9), alprostadil, fosinopril, gremlin, PPAR-gamma, TNF-alpha (SEQ ID NO: 10), or combinations thereof. Moreover, in another example, the angiogenic agent, may be present in the mixture with a concentration of between 5 micro molar and 500 micro molar. In some cases, the small molecule drug may be an osteogenic drug, immunosuppressive drug, or combinations thereof. Moreover, the small molecule drug may be present at a molar concentration of between 2 nano molar and 1 molar. The small molecule drug may be selected from Fingolimod, Purmorphamine, 22 (S)-hydroxycholesterol, Mevinolin, Resveratrol, Genistein, Icariin, Metformin, Dexamethasone, Flavonoids, Alendronate, zoledronic acid, Melatonin, TGF-β, vitamin D, bisphosphonates, curcumin, Simvastatin, or combinations thereof. In addition, the anti-inflammatory agent may be selected from aloe vera extract, non-steroidal anti-inflammatory drugs (NSAIDs), corticosteroid, tritrpticin, or combinations thereof. Moreover, the anti-inflammatory agent may be present at the concentration ratio (volume/volume) of between 0.1:1 and 1:1 of the whole mixture.

In another general aspect, the present disclosure is directed to a mixture for an injectable scaffold. The mixture may include a self-assembling core, an angiogenic agent, a small molecule drug, and an anti-inflammatory agent.

The above general aspect may include one or more of the following features. For example, the mixture may include a (RADA) 4 peptide (SEQ ID NO: 1) including four building blocks of RADA with an amino acid sequence of arginyl (R)-alanyl (A)-aspartyl (D)-alanyl (A) as a self-assembling core, a peptide with an amino acid sequence of seryl-aspartyl-lysyl-proline (SDKP) (SEQ ID NO: 7) as an angiogenic agent, a plurality of Fingolimod nanoemulsion as a small molecule drug, and an aloe vera extract as an anti-inflammatory agent.

In another general aspect, the present disclosure is directed to a method for preparing an in-situ scaffold. The method may include dissolving a plurality of self-assembling core in a solvent to form a first solution, preparing a nanoemulsion of Fingolimod, mixing the nanoemulsion of Fingolimod and an additive with the first solution to form a second solution, and applying the second solution to a bone defect site to form a gel as an in-situ scaffold.

The above general aspect may include one or more of the following features. For example, the additive may include an angiogenic agent, a small molecule drug, an anti-inflammatory agent, or combinations thereof. Moreover, preparation of the Fingolimod nanoemulsion may include dissolving a plurality or a first amount of Fingolimod in an oily material to form a Fingolimod solution, adding a surfactant, water, and a co-surfactant to the Fingolimod solution to form a mixture, and stirring the mixture to form a nanoemulsion of Fingolimod. In some cases, the Fingolimod may be present in the nanoemulsion with a concentration of between 2 nano molar and 1 molar. Furthermore, the oily material may be selected from the group consisting of paraffin, soybean oil, oleic acid, *eucalyptus* oil, plant oils, or combinations thereof. In another example, the surfactant may be polyethylene glycol (PEG), lecithin, Tween 20, Tween 80, Span 80, or combinations thereof. Moreover, the co-surfactant may include methanol, ethanol, isopropyl alcohol, butanol, pentanol, or combinations thereof.

In another general aspect, the present disclosure is directed to a method for treating bone defects by administering a therapeutically effective amount of the present mixture to the defect site.

Other systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the implementations, and be protected by the following claims.

BRIEF DESCRIPTION OF THE DRAWINGS

The drawing figures depict one or more implementations in accord with the present teachings, by way of example only, not by way of limitation. In the figures, like reference numerals refer to the same or similar elements.

FIG. 1 illustrates a method for preparing a mixture of an in-situ scaffold, according to an implementation of the present disclosure;

DETAILED DESCRIPTION

Figure 2:
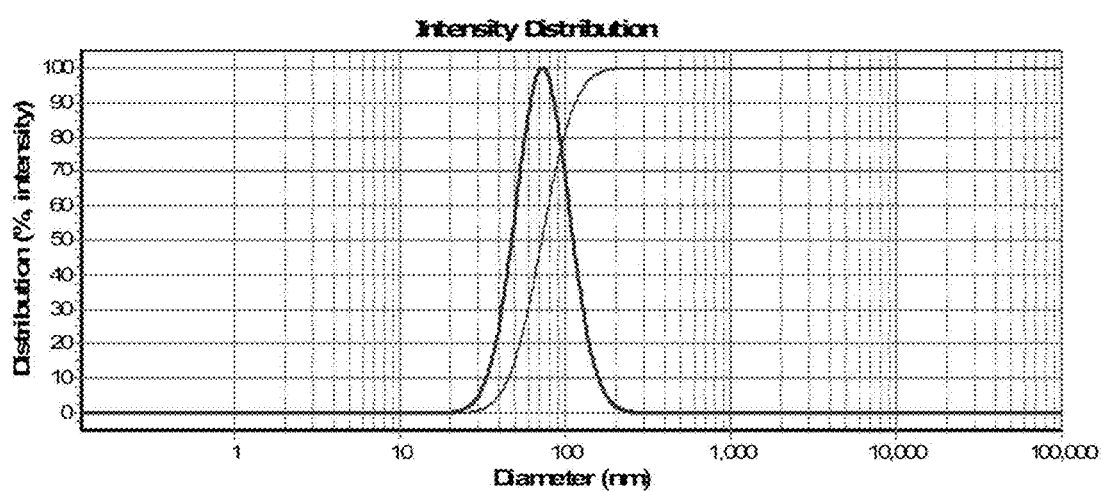
FIG. 2 illustrates a graph with particle size analysis of the Fingolimod nanoemulsion by dynamic light scattering (DLS) method, according to an implementation of the present disclosure.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The mixtures and methods disclosed herein are directed to the use of self-assembling peptides in combination with a bioengineering platform. The disclosed implementations are proposed to assist functional bone regeneration in cases of bone defects, including exposed fractures due to trauma and spinal cord disorders. In one implementation, a mixture for an injectable scaffold with anti-inflammatory, angiogenic, and osteogenic properties is disclosed. The base of the scaffold is a self-assembling peptide nanofiber having a hydrogel based structure. Some additives can be embedded in the scaffold in order to increase the efficiency of bone healing in different bone defects such as spinal cord injury and maxillofacial fractures. In another general aspect, the present disclosure describes a method for preparing an in-situ scaffold, as well as a preparation method for the Fingolimod nanoemulsion. The present disclosure also describes cytotoxicity and osteogenesis tests performed on different implementations of the mixture of injectable scaffold.

In different implementations, biomimetic self-assembling peptide scaffolds may enhance tissue regeneration into natural tissues by creation of biological substitutes for defective organs. In some implementations, self-assembling peptides can be used for in vitro applications for cell 3D culture as well as in vivo for tissue regeneration, for example in addressing as bone defects.

In one implementation, the present disclosure is directed to a mixture for an injectable scaffold with anti-inflammatory, angiogenic, and osteogenic properties. In some implementations, the base of the present scaffold is a self-assembling core with a hydrogel based structure. For example, the core may comprise a hydrogel based structure of peptide nanofibers. In different implementations, additives may be embedded in the scaffold in order to increase the efficiency of bone healing in different bone defects such as spinal cord injury and maxillofacial fractures. For example, such additives can include angiogenic agents, small molecule drugs, and/or anti-inflammatory agents.

In some implementations, the self-assembling core of the mixture may comprise a (RADA)4 peptide (SEQ ID NO: 1) including four building blocks of RADA. The RADA (SEQ ID NO: 1) may be understood to refer to an amino acid sequence that comprises one or more of arginyl(R)-alanyl (A)-aspartyl (D)-alanyl (A), as well as KSL peptide (SEQ ID NO: 2), EAK peptide (SEQ ID NO: 3), KQL peptide (SEQ ID NO: 4), ESL peptide (SEQ ID NO: 5), EQL peptide (SEQ ID NO: 6), or combinations thereof. Also, in some implementations, the concentration ratio (weight/volume) of the self-assembling core may be between 0.125 (w/v) and 2 (w/v) of the volume of the whole mixture. In one implementation, the self-assembling core may include a plurality of self-assembling peptide nanofibers.

Moreover, in different implementations, the angiogenic agent may be selected from SDKP peptide (SEQ ID NO: 7), VEGF (SEQ ID NO: 8), PGE1 (SEQ ID NO: 9), alprostadil, fosinopril, gremlin, PPAR-gamma, TNF-alpha (SEQ ID NO: 10), or combinations thereof. In addition, in some implementations, the angiogenic agent may be present in the mixture with a concentration between 5 micro molar and 500 micro molar.

As disclosed herein the small molecule drug may be an osteogenic drug, immunosuppressive drug, or combinations thereof. In some implementations, the small molecule drug may be selected from Fingolimod, Purmorphamine, 22

(S)-hydroxycholesterol, Mevinolin, Resveratrol, Genistein, Icariin, Metformin, Dexamethasone, Flavonoids, Alendronate, zoledronic acid, Melatonin, TGF-β, vitamin D, bisphosphonates, curcumin, Simvastatin, or combinations thereof. Also, in different implementations, the small molecule drug may be present at a molar concentration of between 2 nano molar and 1 molar.

According to some implementations, the anti-inflammatory agent may be selected from aloe vera extract, non-steroidal anti-inflammatory drugs (NSAIDs), corticosteroid, tritrpticin, or combinations thereof. Moreover, in different implementations the anti-inflammatory agent may be present at the concentration ratio (volume/volume) of between 0.1:1 and 1:1 of the whole mixture.

Referring now to FIG. 1, an example of one method 100 for preparing the mixture of the injectable scaffold is presented in a flow chart, according to one or more aspects of the present disclosure. Method 100 may include a first step 101 of dissolving a plurality of self-assembling peptide in a solvent to form a first solution; a second step 102 of preparing a nanoemulsion of small molecule drug (for example, Fingolimod); a third step 103 of mixing the nanoemulsion of Fingolimod and an additive with the first solution to form a second solution; and a fourth step 104 of applying the second solution to the defect site to form a gel as an in-situ scaffold.

For purposes of clarity, additional details with reference to FIG. 1 are provided below. As noted above, in first step 101, a plurality of self-assembling core may be dissolved in a solvent to form a first solution. In some implementations, the solvent may be an isotonic solution such as one comprising 10% glucose solution (weight/volume), 10% sucrose solution (weight/volume), and/or 10% dextrose solution (weight/volume). Moreover, in some implementations, the self-assembling core may be present in the first solution with a concentration (weight/volume) of about between 0.125% (w/v) and 2% (w/v).

Furthermore, in second step 102, a nanoemulsion with a small molecule drug may be prepared. In some implementations, a measure of Fingolimod may initially be dissolved in a substantially oily substance or fluid including oil by stirring to form a Fingolimod solution. In one implementation, the solution can be stirred until it is substantially uniform or homogenous. While the solution is stirred or mixed together, a surfactant and/or water may be added. In addition, a plurality of co-surfactant may be subsequently added to the Fingolimod solution to form an oil in water (o/w) nanoemulsion of Fingolimod.

According to some implementations, the Fingolimod or other small drug molecule may be present in the nanoemulsion with a concentration of between about 2 nanomolar and 1 molar. The oily material may be selected from the group consisting of paraffin, soybean oil, oleic acid, eucalyptus oil, plant oils, or combinations thereof. Moreover, in one implementation, the oily material may be present in an amount of about 2 percent of the final volume of the nanoemulsion.

According to some implementations, the surfactant may include polyethylene glycol (PEG), lecithin, Tween 20, Tween 80, Span 80, or combinations thereof. Also, the surfactant may be present in an amount of about 6 percent of the final volume of the nanoemulsion in one implementation, though in other implementations, the surfactant can range from 3 percent to 10 percent of the final volume.

According to some implementations, the co-surfactant may be selected from the group consisting of methanol, ethanol, isopropyl alcohol, butanol, pentanol, or combinations thereof. Moreover, the co-surfactant may be present in an amount of about 1 percent of the final volume of the nanoemulsion in one implementation, though in other implementations, the co-surfactant can range from 0.5 percent to 5 percent of the final volume.

Generally, Fingolimod is understood to comprise a light-sensitive material. Thus, in some implementations, preparation of the Fingolimod nanoemulsion may occur in a dark environment. Furthermore, stirring or mixing of the Fingolimod solution may utilize a magnet stirrer, a homogenizer, an ultrasound device, or combinations thereof. In one implementation, the final Fingolimod nanoemulsion may comprise a particle size between about 40 nanometers and 400 nanometers, and its polydispersity index (PDI) may be up to 0.5.

With reference again to FIG. 1, in third step 103, the second solution may be prepared by mixing the nanoemulsion of Fingolimod, and an additive with the first solution, and the additive may include an angiogenic agent, a small molecule drug, an anti-inflammatory agent, or combinations thereof.

According to some implementations, the Fingolimod (or other small molecule drug) nanoemulsion may be present in the second solution with a concentration of between about 2 nanomolar and 1 molar. The angiogenic agent may be selected from the group consisting of SDKP peptide (SEQ ID NO: 7), VEGF (SEQ ID NO: 8), PGE1 (SEQ ID NO: 9), alprostadil, fosinopril, gremlin, PPAR-gamma, TNF-alpha (SEQ ID NO: 10), or combinations thereof, and may be present in the mixture at a molar concentration of between 5 micro molar and 500 micro molar.

In addition, in different implementations, the small molecule drug may be an osteogenic drug, immunosuppressive drug, or combinations thereof, and the small molecule drug may be selected from Fingolimod, Purmorphamine, 22 (S)-hydroxycholesterol, Mevinolin, Resveratrol, Genistein, Icariin, Metformin, Dexamethasone, Flavonoids, Alendronate, zoledronic acid, Melatonin, TGF-β, vitamin D, bisphosphonates, curcumin, Simvastatin, or combinations thereof. In one implementation, the small molecule drug may be present at a molar concentration of between 2 nano molar and 1 molar.

According to some implementations, the anti-inflammatory agent may be selected from aloe vera extract, non-steroidal anti-inflammatory drugs (NSAIDs), corticosteroid, tritrpticin, or combinations thereof. Moreover, in one implementation, the anti-inflammatory agent may be present at the concentration ratio (volume/volume) of between 0.1:1 and 1:1 of the whole mixture.

Furthermore, with reference to FIG. 1, in fourth step 104, the second solution may be applied to the defect site to form a gel as an in-situ scaffold. In some implementations, this injectable scaffold may be formed in-situ upon interaction of the self-assembling core solution with biological fluids in a sol-gel process. Therefore, a hydrogel based structure with the self-assembling peptide nanofibers may be formed in the defect site.

EXAMPLES

The following examples describe different implementations of the preparation method of the injectable scaffold of the present disclosure. The following examples further describe a cytotoxicity assay and osteogenesis assay performed on the present injectable scaffold.

Example 1: Preparation of the Mixture of the Injectable Scaffold

In this example, a mixture of an injectable scaffold was prepared through the following steps. A first solution was prepared by dissolving a plurality of self-assembling peptide in a solvent as follows. Initially, a plurality of self-assembling (RADA) 4 peptide (SEQ ID NO: 1) including four building blocks of RADA with an amino acid sequence of arginyl(R)-alanyl (A)-aspartyl (D)-alanyl (A) was dissolved in a sucrose solution with a concentration of about 10% (weight/volume) to form a first solution. The (RADA) 4 peptide (SEQ ID NO: 1) concentration in the first solution was about 0.125% (weight/volume) of the whole volume of the first solution.

In the next step, an oil in water (o/w) nanoemulsion of Fingolimod was prepared as follows. Fingolimod is a light-sensitive material; therefore, the Fingolimod nanoemulsion was prepared in a dark environment. A plurality of Fingolimod was first dissolved in a paraffin oil through stirring to form a Fingolimod solution with a concentration of about 250 microgram per milliliter. The oily material was present in an amount of about 2 percent of the final volume of the nanoemulsion.

Subsequently, while stirring the solution, a plurality of Tween 80 and Span 80 as surfactants and water were added to the Fingolimod solution; finally, a plurality of ethanol as a co-surfactant were added to the Fingolimod solution to form an oil in water (o/w) nanoemulsion of Fingolimod. The Tween 80 and Span 80 were present in an amount of about 2% and 4% of the final volume of the nanoemulsion, respectively. Also, ethanol was present in an amount of about 1 percent of the final volume of the nanoemulsion.

The Fingolimod solution was stirred by exposure of the solution to ultrasound radiation with a power of 400 Watt and for a duration of about 15 minutes. FIG. 2 is a graph presenting a particle size analysis of the prepared Fingolimod nanoemulsion by a dynamic light scattering method. Referring to FIG. 2, it can be seen from the peak of the graph that the mean particle size of the Fingolimod nanoemulsion was about 72.47±7.74 nanometers. Also, a polydispersity index (PDI) of the particles in the Fingolimod nanoemulsion is about 0.17.

In a following step, a plurality of the nanoemulsion of Fingolimod, a plurality of angiogenic peptide with an amino acid sequence of seryl-aspartyl-lysyl-proline (SDKP) (SEQ ID NO: 7), and a plurality of aloe vera extract as an anti-inflammatory agent were mixed with the first solution to form a second solution.

The final concentration of the Fingolimod in the second solution was about 40 nanogram per milliliter. The SDKP peptide (SEQ ID NO: 7) was present in the mixture at a molar concentration of about 75 micro molar. Moreover, the aloe vera extract was present at the concentration ratio (volume/volume) of about 0.2:1 of the whole mixture.

Finally, the second solution was applied to a defect site to form a gel as an in-situ scaffold for tissue regeneration. This injectable scaffold was formed in-situ upon interaction of the (RADA)4 peptide (SEQ ID NO: 1) solution with biological fluids in a sol-gel process.

Example 2: Cytotoxicity Assay of the Injectable Scaffold

In some cases, lactate dehydrogenase (LDH) assays can be performed by assessing or measuring the LDH released into the media as a marker of dead cells. In this example, biocompatibility and cytotoxicity of the injectable scaffold of the present disclosure as a whole and its components were measured by an LDH cytotoxicity assay as follows.

Figure 3:
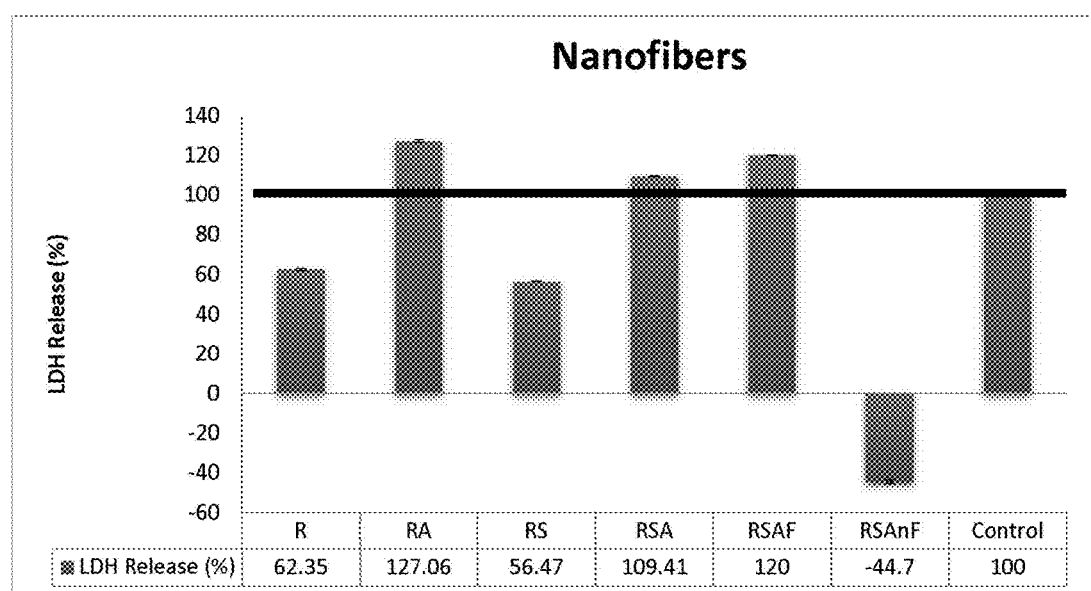
FIG. 3 illustrates data of LDH release from Mg-63 cells of six test groups and one control group, according to an implementation of the present disclosure.

Mg-63 cell line was the source of osteoblast cells in the following assays. Six test groups and one control group of Mg-63 cells were prepared for investigating the cytotoxicity effects of the present injectable scaffold and its components. FIG. 3 illustrates the data of LDH release from Mg-63 cells of six test groups and one control group.

Referring to FIG. 4, test groups were treated and identified as follows: (1) a group treated with only (RADA)4 peptide (SEQ ID NO: 1) nanofibers and designated by the letter "R"; (2) a group treated with both (RADA)4 peptide (SEQ ID NO: 1) nanofibers and aloe vera extract and designated by the letters "RA"; (3) a group treated with both (RADA)4 peptide (SEQ ID NO: 1) nanofibers and SDKP peptide (SEQ ID NO: 7) and designated by the letters "RS"; (4) a group treated with (RADA)4 peptide (SEQ ID NO: 1) nanofibers, aloe vera extract and SDKP peptide (SEQ ID NO: 7) and designated by the letters "RSA"; (5) a group treated with (RADA)4 peptide, aloe vera extract, SDKP peptide and Fingolimod hydrochloride and designated by the letters "RSAF"; and (6) a group treated with (RADA)4 peptide (SEQ ID NO: 1) nanofibers, aloe vera extract, SDKP peptide (SEQ ID NO: 7) and Fingolimod nanoemulsion and designated by the letters "RSAnF".

As illustrated in FIG. 3, the result of the LDH cytotoxicity assays showed significantly less cell membrane damage in the "RSAnF" group treated with (RADA)4 peptide (SEQ ID NO: 1) nanofibers, aloe vera extract, SDKP peptide (SEQ ID NO: 7) and Fingolimod nanoemulsion as compared to the other test groups as well as the control group.

Furthermore, with respect to the "RA" test group, which was treated with (RADA)4 peptide (SEQ ID NO: 1) nanofibers and aloe vera extract with a concentration of 5% (volume/volume) of the whole mixture, with an LDH release of about 127.06%, the cytotoxicity was significantly greater relative to the "R" group, which had an LDH release of about 62.35%, due to the cell membrane damage of the aloe vera extract (P<0.01). Furthermore, the cytotoxicity of the "RA" test group is higher than the control ("R") group.

Referring to the "RS" group, which was treated with (RADA)4 peptide (SEQ ID NO: 1) nanofibers and SDKP peptide (SEQ ID NO: 7) with a concentration of about 75 micrograms per milliliter, with an LDH release of about 56.47%, the cytotoxicity was significantly smaller as compared to the "RA" group (P<0.01). In addition, in the "RSA" group which was treated with (RADA)4 peptide (SEQ ID NO: 1) nanofibers, the aloe vera extract and the SDKP peptide (SEQ ID NO: 7), with an LDH release of about 109.41%, the cell membrane damage was significantly greater as compared to both the "R" group and "RS" group (P<0.05). Furthermore, the "RSA" group results were greater than that of the control group.

In the "RSAF" group, which was treated with (RADA)4 peptide (SEQ ID NO: 1) nanofibers, the aloe vera extract, the SDKP peptide (SEQ ID NO: 7), and the Fingolimod hydrochloride with a concentration of about 10 nanogram per milliliter, with an LDH release of about 120%, the cell membrane damage was significantly higher than the "R" group (P<0.05). In addition, the cytotoxicity result for the "RSAF" group was higher than that of the control group.

However, with respect to the "RSAnF" group, which was treated with (RADA)4 peptide (SEQ ID NO: 1) nanofibers, the aloe vera extract, the SDKP peptide (SEQ ID NO: 7), and the Fingolimod nanoemulsion, with an LDH release of about −44.7%, it can be seen that the LDH release was significantly lower than other groups. In addition, this combination has a significantly lower amount of cell membrane damage and cytotoxicity effects as compared to the control group, which has an LDH release of 100%.

Example 3: Osteogenesis Assay of the Injectable Scaffold

In this example, osteogenesis of the injectable scaffold was evaluated by measuring the calcium deposition of the test groups. At first, mesenchymal stem cells (MSCs), C2C12 cells as pre-myoblastic mesenchymal stem cells, and bone marrow mesenchymal stem cells were chosen for osteoblast differentiation. These cells were used as reference cells for the study of osteogenesis because BMP-2 expression in these cells is minimal.

The cells were cultured in a basal medium and an osteogenic medium in six test groups and one control group for a duration of 14 days. They were then stained with Alizarin Red dye. Alizarin Red was used in a biochemical assay to determine the presence of calcific deposition by cells of an osteogenic lineage quantitatively by colorimetry.

The calcium deposition is an early stage marker of matrix mineralization, and a crucial step towards the formation of calcified extracellular matrix associated with osteogenesis. In this example, calcium deposition can be achieved in two processes including osteoinduction and osteoconduction.

For purposes of this application, osteoinduction refers to the process in which osteogenesis and calcium deposition are obtained due to the effect of the scaffold treatment in a basal medium and in the absence of the osteogenic medium. Osteoconduction refers to the process where osteogenesis and calcium deposition is obtained due to the effects of the scaffold treatment in an osteogenic medium.

Figure 4A:
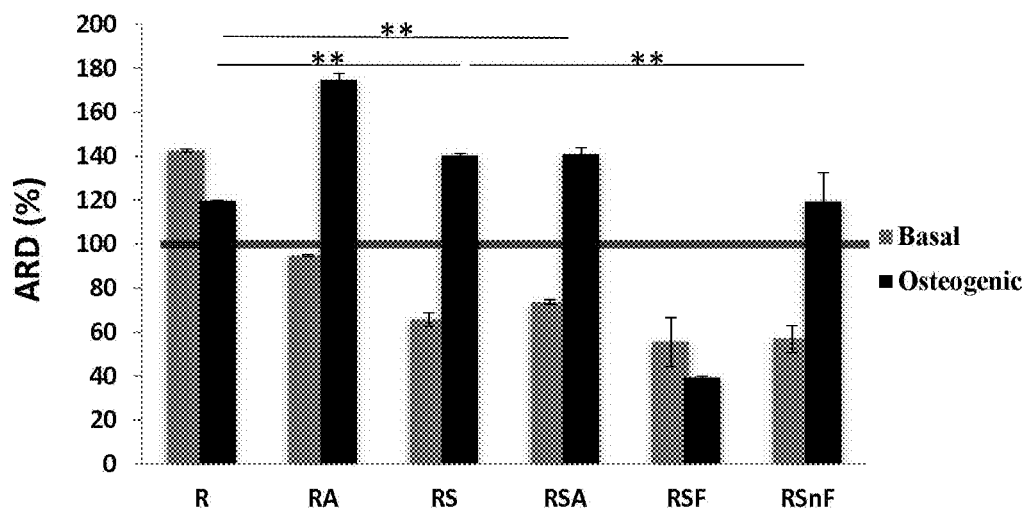
FIG. 4A illustrates percentages of a concentration ratio of Alizarin red dye present in the test groups and the control group after Alizarin red staining, according to an implementation of the present disclosure.

FIG. 4A illustrates the percentage of a concentration ratio of Alizarin red dye present in the test groups and the control group after Alizarin red staining, as a standard of calcium deposition of cells cultured on a basal medium and an osteogenic medium, according to an exemplary implementation of the present disclosure.

Test groups in this example were treated as follows: (1) a group treated with only (RADA)4 peptide (SEQ ID NO: 1) nanofibers and designated by the letter "R"; (2) a group treated with (RADA)4 peptide (SEQ ID NO: 1) nanofibers and aloe vera extract and designated by the letters "RA"; (3) a group treated with (RADA)4 peptide (SEQ ID NO: 1) nanofibers and SDKP peptide (SEQ ID NO: 7) and designated by the letters "RS"; (4) a group treated with (RADA)4 peptide (SEQ ID NO: 1) nanofibers, aloe vera extract and SDKP peptide (SEQ ID NO: 7) and designated by the letters "RSA"; (5) a group treated with (RADA)4 peptide (SEQ ID NO: 1), SDKP peptide (SEQ ID NO: 7), and Fingolimod hydrochloride and designated by the letters "RSF"; and (6) a group treated with (RADA)4 peptide (SEQ ID NO: 1) nanofibers, SDKP peptide (SEQ ID NO: 7) and Fingolimod nanoemulsion and designated by the letters "RSnF".

The "RA" test group was treated with (RADA)4 peptide (SEQ ID NO: 1) nanofibers and the aloe vera extract with a concentration of 5% (volume/volume) of the whole mixture, and the "R" group was treated with only (RADA)4 peptide (SEQ ID NO: 1) nanofibers. As shown in FIG. 4A, the addition of the aloe vera extract in the "RA" group decreased the osteoinduction and significantly increased the osteoconduction in the "RA" group (P<0.001) relative to the "R" group.

In addition, the "RS" test group was treated with (RADA)4 peptide (SEQ ID NO: 1) nanofibers and the SDKP peptide (SEQ ID NO: 7) with a concentration of about 75 micrograms per milliliter, and the "R" group was treated with only (RADA)4 peptide (SEQ ID NO: 1) nanofibers. In FIG. 4A, it can be seen that the addition of the the SDKP peptide (SEQ ID NO: 7) in the "RS" group resulted in the loss of the osteoinduction and significantly increased the osteoconduction in the "RS" group (P<0.001) relative to the "R" group. However, addition of the aloe vera extract increased the osteoconduction more than addition of the SDKP peptide (SEQ ID NO: 7).

The "RSA" group the cells were treated with the aloe vera extract and the SDKP peptide (SEQ ID NO: 7) simultaneously alongside of the (RADA)4 peptide (SEQ ID NO: 1) nanofibers. As shown in FIG. 4A, there was not a significant difference in the osteoinduction and osteoconduction of the "RSA" group in comparison to the "RS" group.

Referring again to FIG. 4A, in the "RSF" group, addition of the Fingolimod hydrochloride to the SDKP peptide (SEQ ID NO: 7) and the (RADA)4 peptide (SEQ ID NO: 1) nanofiber significantly decreased the osteoinduction and osteoconduction. Furthermore, these results were lower than that of the control group.

On the other hand, referring to the results of the "RSnF" group, it can be seen that changing the form of the Fingolimod into the nanoemulsion improved the osteoconduction of the test group. In other words, the results of Alizarin red staining show that the Fingolimod nanoemulsion significantly improved osteogenesis as compared to the soluble form of the Fingolimod in the "RSF" group.

Figure 4B:
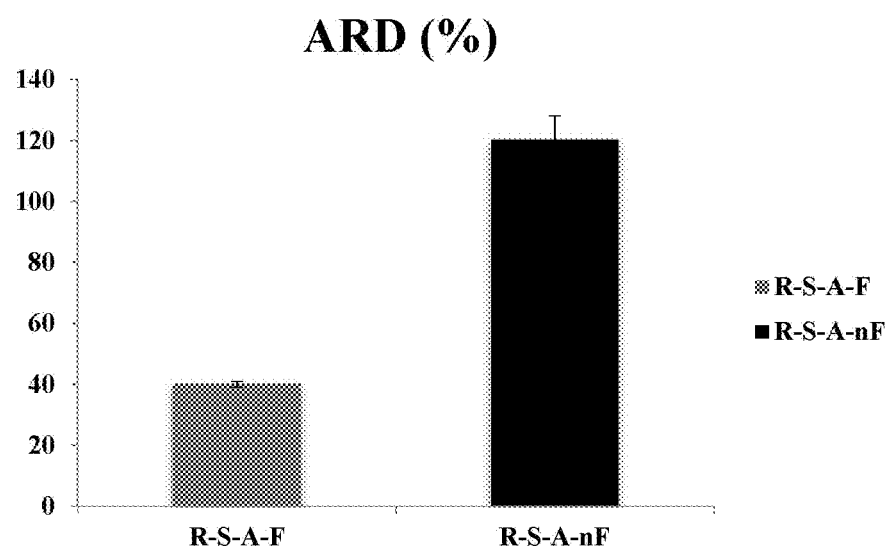
FIG. 4B illustrates the percentages of a concentration ratio of Alizarin red dye present in cells of two test groups after Alizarin red staining, according to an implementation of the present disclosure.

Referring next to FIG. 4B, percentage of a concentration ratio of Alizarin red dye present in cells of two test groups after Alizarin red staining as a standard of calcium deposition of mesenchymal stem cells (MSCs) is presented, according to an exemplary implementation of the present disclosure.

Test groups were treated as follows: (1) a group treated with (RADA)4 peptide (SEQ ID NO: 1) nanofibers, SDKP peptide (SEQ ID NO: 7), aloe vera extract, and Fingolimod hydrochloride and designated by the letters "R-S-A-F"; and (2) a group treated with (RADA)4 peptide (SEQ ID NO: 1) nanofibers, SDKP peptide (SEQ ID NO: 7), aloe vera extract, and Fingolimod nanoemulsion and designated by the letters "R-S-A-nF".

Referring to FIG. 4B, a comparison between the data of Alizarin red staining of the "RSAF" group and the "RSAnF" group shows that changing the form of the Fingolimod into the nanoemulsion has induced higher calcium deposition in the osteoblast cells differentiated from mesenchymal stem cells (MSCs). Therefore, presence of the Fingolimod in a nanoemulsion form significantly improved osteogenesis compared to the soluble form of the Fingolimod in the "RSAF" group.

Figure 5A:
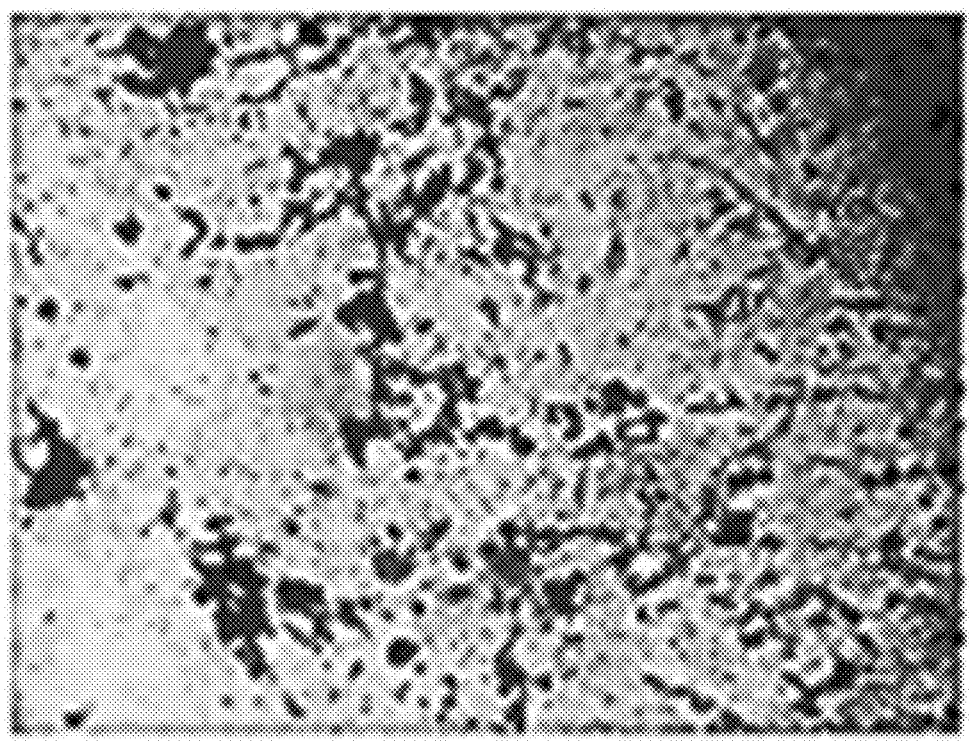
FIG. 5A illustrates an optical image of the osteoblast-like cells of test group "RSF" treated (RADA)4 peptide (SEQ ID NO: 1) nanofibers, SDKP peptide (SEQ ID NO: 7), and Fingolimod hydrochloride after Alizarin red staining, according to an implementation of the present disclosure.

FIG. 5A depicts an optical image of the osteoblast-like cells of test group "RSF" treated (RADA)4 peptide (SEQ ID NO: 1) nanofibers, SDKP peptide (SEQ ID NO: 7), and Fingolimod hydrochloride after Alizarin red staining, according to an exemplary implementation of the present disclosure. In addition, FIG. 5B provides an optical image of the osteoblast-like cells of test group "RSnF" treated (RADA)4 peptide (SEQ ID NO: 1) nanofibers, SDKP peptide (SEQ ID NO: 7), and Fingolimod nanoemulsion after Alizarin red staining, according to an exemplary implementation of the present disclosure.

Figure 5B:
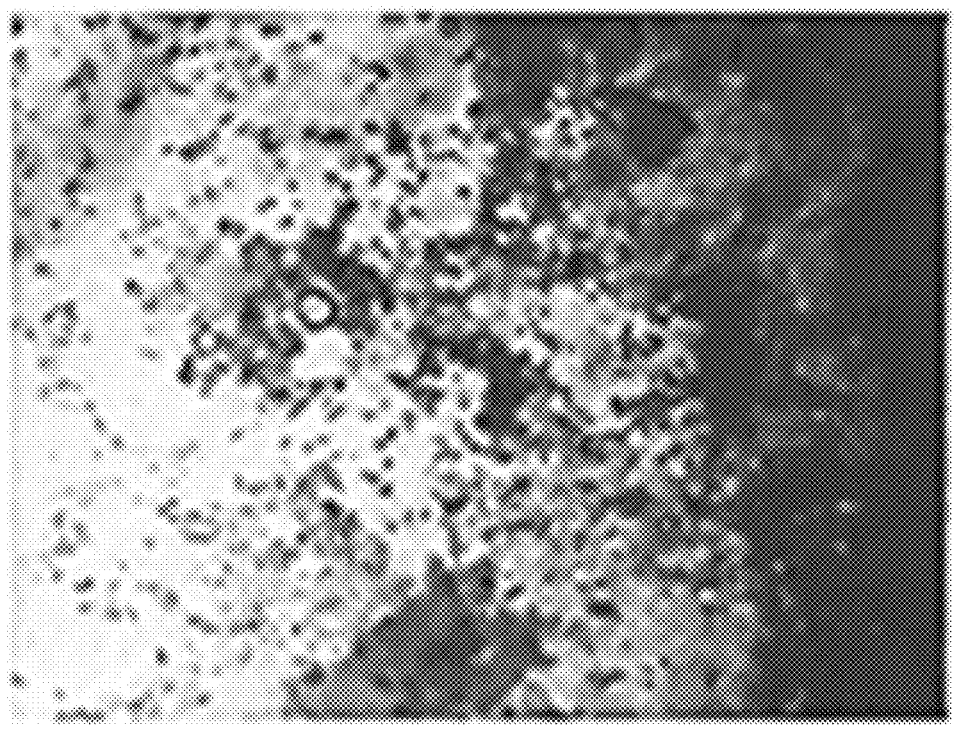
FIG. 5B illustrates an optical image of the osteoblast-like cells of test group "RSnF" treated (RADA)4 peptide (SEQ ID NO: 1) nanofibers, SDKP peptide (SEQ ID NO: 7), and Fingolimod nanoemulsion after Alizarin red staining, according to an implementation of the present disclosure.

In FIGS. 5A and 5B, the black dots refer to the calcium deposition of the test groups, which were cultured in the osteogenic medium. As shown in the images, the calcium deposition in the test group of "RSnF" containing Fingolimod nanoemulsion is significantly higher than calcium deposition of the "RSF" test group containing Fingolimod hydrochloride.

In different implementations, the (RADA)4 self-assembled peptide (SEQ ID NO: 1) scaffold with the SDKP peptide (SEQ ID NO: 7), the aloe vera extract, and Fingolimod nanoemulsion as a potential bone substitute can be used with great efficacy in the maxillofacial and vertebral column of a patient. In such cases, it may not be necessary to implant the scaffold by surgery. By injecting the scaffold in the defect area, the scaffold, with a sustained release of various substances such as angiogenic agent, osteogenic agent, and anti-inflammatory agent, is formed in-situ. After tissue regeneration, this biodegradable scaffold can be converted to amino acid and other safe compounds.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for preparing in-situ scaffolds, comprising:
   dissolving a self-assembling peptide in a solvent to form a first solution;
   preparing a nanoemulsion of Fingolimod with a concentration of Fingolimod between 2 nano molar and 1 molar, comprising:
      dissolving a first amount of Fingolimod in an oily material to form a Fingolimod solution;
      adding a surfactant, water, and a co-surfactant to the Fingolimod solution to form a mixture; and
      stirring the mixture to form a nanoemulsion of Fingolimod;
   mixing the nanoemulsion of Fingolimod and an angiogenic agent with the first solution to form a second solution, the second solution comprising the angiogenic agent with a concentration between 5 micro molar and 500 micro molar.

2. The method of claim 1, wherein the oily material comprises paraffin.

3. The method of claim 1, wherein the surfactant comprises polysorbate 80.

4. The method of claim 1, wherein the co-surfactant comprises ethanol.

5. The method of claim 1, wherein the self-assembling peptide comprises at least one of (RADA)4 peptide (SEQ ID NO: 1), KSL peptide (SEQ ID NO: 2), EAK peptide (SEQ ID NO: 3), KQL peptide (SEQ ID NO: 4), ESL peptide (SEQ ID NO: 5), EQL peptide (SEQ ID NO: 6), or combinations thereof.

6. The method of claim 1, wherein the self-assembling peptide is present in the first solution with a concentration between 0.125% weight/volume (w/v) and 2% w/v.

7. The method of claim 1, wherein the angiogenic agent comprises a SDKP peptide (SEQ ID NO: 7).

* * * * *

SEQUENCE LISTING

```
<160> NUMBER OF SEQ ID NOS: 10

<210> SEQ ID NO 1
<211> LENGTH: 16
<212> TYPE: PRT
<213> ORGANISM: Artificial Sequence
<220> FEATURE:
<223> OTHER INFORMATION: A self-assembling amino acid sequence ((RADA)4
      peptide)

<400> SEQUENCE: 1

Arg Ala Asp Ala Arg Ala Asp Ala Arg Ala Asp Ala Arg Ala Asp Ala
1               5                   10                  15
```

```
<210> SEQ ID NO 2
<211> LENGTH: 10
<212> TYPE: PRT
<213> ORGANISM: Artificial Sequence
<220> FEATURE:
<223> OTHER INFORMATION: A self-assembling amino acid sequence (KSL
      peptide)

<400> SEQUENCE: 2

Lys Lys Val Val Phe Lys Val Lys Phe Lys
1               5                   10

<210> SEQ ID NO 3
<211> LENGTH: 16
<212> TYPE: PRT
<213> ORGANISM: Artificial Sequence
<220> FEATURE:
<223> OTHER INFORMATION: A self-assembling amino acid sequence (EAK
      peptide)

<400> SEQUENCE: 3

Ala Glu Ala Glu Ala Lys Ala Lys Ala Glu Ala Glu Ala Lys Ala Lys
1               5                   10                  15

<210> SEQ ID NO 4
<211> LENGTH: 20
<212> TYPE: PRT
<213> ORGANISM: Artificial Sequence
<220> FEATURE:
<223> OTHER INFORMATION: A self-assembling amino acid sequence (KQL
      peptide)

<400> SEQUENCE: 4

Ala Arg Thr Lys Gln Thr Ala Arg Lys Ser Thr Gly Gly Lys Ala Pro
1               5                   10                  15

Arg Lys Gln Leu
            20

<210> SEQ ID NO 5
<211> LENGTH: 21
<212> TYPE: PRT
<213> ORGANISM: Artificial Sequence
<220> FEATURE:
<223> OTHER INFORMATION: A self-assembling amino acid sequence (ESL
      peptide)

<400> SEQUENCE: 5

Glu Ser Leu Asn Lys Asn Lys His Phe Val Pro Ser Ala Gly Ala Asp
1               5                   10                  15

Ser Glu Thr His Cys
            20

<210> SEQ ID NO 6
<211> LENGTH: 3
<212> TYPE: PRT
<213> ORGANISM: Artificial Sequence
<220> FEATURE:
<223> OTHER INFORMATION: A self-assembling amino acid sequence (EQL
      peptide)

<400> SEQUENCE: 6

Glu Gln Leu
1

<210> SEQ ID NO 7
<211> LENGTH: 4
```

```
<212> TYPE: PRT
<213> ORGANISM: Artificial Sequence
<220> FEATURE:
<223> OTHER INFORMATION: A synthetic tetrapeptide Ac-SDKP (Seraspenide)
      involved in angiogenesis (SDKP peptide)

<400> SEQUENCE: 7

Ser Asp Lys Pro
1

<210> SEQ ID NO 8
<211> LENGTH: 4
<212> TYPE: PRT
<213> ORGANISM: Artificial Sequence
<220> FEATURE:
<223> OTHER INFORMATION: A vascular endothelial growth factor (VEGF)
      family that currently includes VEGF (VEGF-A), VEGF-B, VEGF-C,
      VEGF-D, VEGF-E, and PlGF (1). VEGF and its receptor system, which
      are regulators in the cell signaling of angiogenesis (VEGF)

<400> SEQUENCE: 8

Val Glu Gly Phe
1

<210> SEQ ID NO 9
<211> LENGTH: 3
<212> TYPE: PRT
<213> ORGANISM: Artificial Sequence
<220> FEATURE:
<223> OTHER INFORMATION: A prostaglandin (PGE-1)

<400> SEQUENCE: 9

Pro Gly Glu
1

<210> SEQ ID NO 10
<211> LENGTH: 4
<212> TYPE: PRT
<213> ORGANISM: Artificial Sequence
<220> FEATURE:
<223> OTHER INFORMATION: A cytokine that binds to TNFRSF1A/TNFR1 and
      TNFRSF1B/TNFBR (TNF-alpha)

<400> SEQUENCE: 10

Thr Asn Phe Ala
1
```